US00PP20967P2

(12) United States Plant Patent
Danziger

(10) Patent No.: US PP20,967 P2
(45) Date of Patent: Apr. 27, 2010

(54) ***ARGYRANTHEMUM* PLANT NAMED 'DANARGY27'**

(50) Latin Name: *Argyranthemum frutescens*
Varietal Denomination: DANARGY27

(75) Inventor: Gabriel Danziger, Moshav Nir-Zvi (IL)

(73) Assignee: Danziger "DAN" Flower Farm, Post Beit Dagan (IL)

( * ) Notice: Subject to any disclaimer, the term of this patent is extended or adjusted under 35 U.S.C. 154(b) by 0 days.

(21) Appl. No.: 12/381,442

(22) Filed: Mar. 12, 2009

(51) Int. Cl.
*A01H 5/00* (2006.01)

(52) U.S. Cl. ..... Plt./406

(58) Field of Classification Search ..... Plt./406
See application file for complete search history.

*Primary Examiner*—Annette H Para
(74) *Attorney, Agent, or Firm*—Foley & Lardner LLP

(57) ABSTRACT

A new distinct cultivar of *Argyranthemum* plant named 'DANARGY27' characterized by its compact growth habit; single, inflorescence averaging about 3.5 cm to 4.0 cm in diameter, which are white in color with a yellow eye; and early flowering.

2 Drawing Sheets

Latin name of the genus and species of the claimed plant: *Argyranthemum frutescens.*

Variety denomination: 'DANARGY27'.

BACKGROUND OF THE INVENTION

The present invention relates to a new and distinct cultivar of *Argyranthemum* plant, botanically known as *Argyranthemum frutescens*, of the Compositae family, commonly referred to as the Marguerite Daisy or Dill Daisy, and hereinafter referred to by the variety denomination 'DANARGY27'.

*Argyranthemum*, of the Compositae family, consists of annuals, which are grown in most climate zones in the U.S., and only in zones 9 and 10 if it is a perennial plant.

The new *Argyranthemum* is a product of a planned breeding program conducted by the inventor, Gabriel Danziger, in Moshav Mishmar Hashiva, Israel. The objective of the breeding program was to develop a new *Argyranthemum* cultivar with single inflorescence with unique coloration and upright, above average stem length.

The new *Argyranthemum* cultivar originated from a cross made in a controlled breeding program by the inventor, Gabriel Danziger, in 2007, in Moshav Mishmar Hashiva, Israel, from open pollination of the seed parent, *Argyranthemum frutescens* 'Daizy Crazy Strawberry Pink' (unpatented), by an unknown *Argyranthemum* cultivar. The new *Argyranthemum* DANARGY27 was discovered and selected by the inventor as a single flowering plant within the progeny of the stated cross in a controlled environment in Moshav Mishmar Hashiva, Israel.

Asexual reproduction of the new *Argyranthemum* cultivar by terminal vegetative cuttings was first performed in January of 2008 in Moshav Mishmar Hashiva, Israel, and has demonstrated that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'DANARGY27' which in combination distinguish this *Argyranthemum* as a new and distinct cultivar:

1. compact growth habit;
2. single, inflorescence averaging about 3.5 cm to 4.0 cm in diameter, which are white in color with a yellow eye; and
3. early flowering.

Plants of the new *Argyranthemum* 'DANARGY27' differ from plants of the seed parent, *Argyranthemum frutescens* 'Daisy Crazy Strawberry Pink' (unpatented), by the characteristics described in Table 1.

TABLE 1

| Characteristic | New Cultivar 'DANARGY27' | Female Parent 'Daisy Crazy Strawberry Pink' (unpatented) |
|---|---|---|
| Plant shape: | Globular | Globular |
| Plant size: | Height: About 30 cm<br>Spread: About 35 cm | Height: About 35 cm<br>Spread: About 40 cm |
| Inflorescence size: | Depth: About 1.5 cm<br>Diameter: About 3.5-4.0 cm | Depth: About 1.5 cm<br>Diameter: About 4.5-5.0 cm |
| Inflorescence color | White with yellow eye | Pink with yellow eye |
| Leaf size: | Length: About 5.5-6.0 cm<br>Width: About 2.0 cm | Length: About 5.5-6.0 cm<br>Width: About 3.0 cm |
| Leaf color: | Green, RHS 137C | Green, RHS 139B |

Of the many commercial cultivars known to the present inventor, the most similar in comparison to the new *Argyranthemum frutescens* 'DANARGY27' is *Argyranthemum frutescens* 'DANARNEP' (patented, U.S. Plant Pat. No. 13,719). Plants of 'DANARGY27' differ from plants of 'DANARNEP' by the characteristics described in Table 2:

TABLE 2

| Characteristic | New Cultivar 'DANARGY27' | Comparison Cultivar 'DANARNEP' (patented U.S. Plant Pat. No. 13,719) |
|---|---|---|
| Plant shape: | Globular | Globular |
| Plant size: | Height: About 30 cm<br>Spread: About 35 cm | Height: About 30-35 cm<br>Spread: About 30-35 cm |
| Inflorescence size: | Depth: About 1.5 cm<br>Diameter: About 3.5-4.0 cm | Depth: About 0.4-0.5 cm<br>Diameter: About 4.0-4.3 cm |
| Leaf size: | Length: About 5.5-6.0 cm<br>Width: About 2.0 cm | Length: About 6.5-7.0 cm<br>Width: About 4.0-4.5 cm |
| Leaf color: | Green, RHS 137C | Green, RHS 137B |

BRIEF DESCRIPTION OF THE PHOTOGRAPHS

The accompanying photographs illustrate the overall appearance of the new *Argyranthemum* cultivar 'DANARGY27' showing the colors as true as is reasonably possible with colored reproductions of this type. Colors in the photographs may differ slightly from the color value cited in the detailed botanical description which accurately describe the color of 'DANARGY27'.

DETAILED BOTANICAL DESCRIPTION

Figure 1:
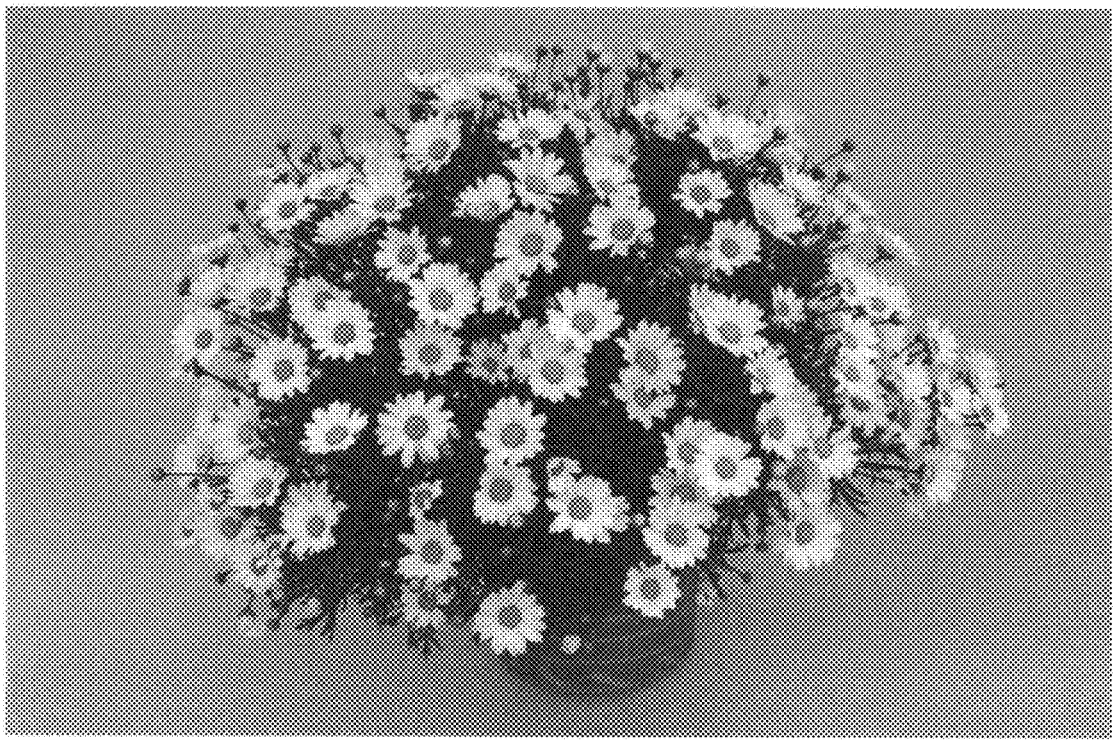
FIG. 1 shows a side view perspective a typical flowering plant of 'DANARGY27' in a 12 cm pot, at 10 weeks of age.
Figure 2:
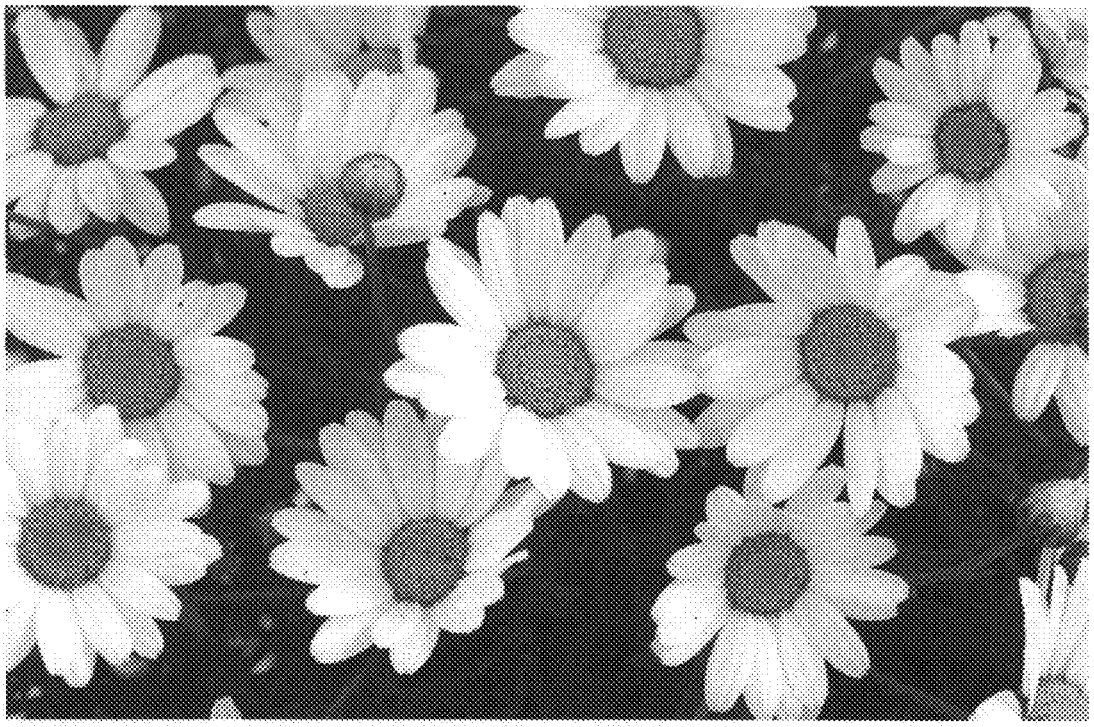
FIG. 2 shows a close-up view of the typical flowers and buds of 'DANARGY27', at 10 weeks of age.

The new *Argyranthemum* cultivar 'DANARGY27' has not been observed under all possible environmental conditions. The phenotype of the new cultivar may vary with variations in environment such as temperature, light intensity, and day-length, without any change in the genotype of the plant.

The aforementioned photographs, together with the following observations, measurements and values describe plants of the new *Argyranthemum* 'DANARGY27' as grown in a greenhouse in Moshav Mishmar Hashiva, Israel, under conditions which closely approximate those generally used in commercial practice.

Color references are made to The Royal Horticultural Society Colour Chart (R.H.S.), 2001 Edition, except where general colors of ordinary significance are used. Color values were taken under daylight conditions at approximately 12:00 noon in Moshav Mishmar Hashiva, Israel. The age of the plant described is 3 months.

Botanical classification: *Argyranthemum frutescens.*

Parentage:

*Seed parent.*—*Argyranthemum frutescens* 'Daisy Crazy Strawberry Pink' (unpatented).

*Pollen parent.*—Unknown *Argyranthemum* cultivar.

Optimal growth conditions:

*Light intensities.*—Full sunlight or slight shade.

*Temperature.*—Day: 16° C. to 23° C. Night: 8° C. to 12° C.

*Temperature tolerance.*—Tolerant to a low temperature of about 5° C. and tolerant to a high temperature of about 27° C.

*Fertilization.*—A balanced fertilizer with level of 100 ppm Nitrogen.

*Growth regulators.*—Unnecessary.

Propagation:

*Type.*—Tip cuttings of side shoots.

*Time and temperature to initiate roots.*—About 7 to 10 days at 18° C. to 20° C.

*Time and temperature to produce a rooted cutting.*—About 14 days at 20° C. to 25° C.

*Rooting description.*—Fine, fibrous and white, RHS N999D in color.

*Rooting habit.*—Freely branching, dense.

Plant description:

*General appearance and form.*—Perennial plant with upright flowers, mounding (globular) plant habit.

*Growth and branching habit.*—Freely branching with lateral flowering branches forming at every node; dense and bushy. No pinching required.

*Growth rate/vigor.*—Strong.

*Plant height.*—About 30 cm.

*Plant width (spread).*—About 35 cm.

*Plant strength.*—Sturdy, upright stems.

*Crop time to produce a mature flowering plant.*—After rooting, about 8 to 10 weeks are required to produce finished flowering plants in 12 cm pots.

Branches:

*Number of branches per plant.*—30–40 primary, 100–150 secondary.

*Length.*—Primary: About 17 cm. Secondary: About 10 cm (including flower).

*Diameter.*—Primary: About 0.5 cm. Secondary: About 0.3 cm.

*Internode length.*—Primary: About 4 cm. Secondary: About 3 cm.

*Aspect.*—Primary: 90°. Secondary: 45°.

*Texture.*—Primary: Smooth. Secondary: Smooth.

*Pubescence.*—Primary: None. Secondary: None.

*Color.*—Primary: Upper surface: Green, RHS 138B. Lower surface: Yellow-green, RHS 144C. Secondary: Upper surface: Green, RHS 138B. Lower surface: Yellow-green, RHS 144C.

Foliage description:

*Arrangement.*—Alternate.

*Length.*—About 5.5 cm to 6 cm.

*Width.*—About 2 cm.

*Overall shape of leaf.*—Pinnatipartite.

*Shape at apex.*—Rounded.

*Shape at base.*—Wedge-shaped.

*Margin.*—Serrate.

*Texture.*—Upper surface: Slightly warty. Lower surface: Slightly warty.

*Pubescencce.*—Upper surface: None. Lower surface: None.

*Color of developing foliage.*—Upper surface: Green, RHS 137C. Lower surface: Green1, RHS 137D.

*Color of mature foliage.*—Upper surface: Green, RHS 137B. Lower surface: Green, RHS 137C.

*Venation pattern.*—Parallel.

*Venation color.*—Upper surface: Green, RHS 137C. Lower surface: Green, RHS 137D.

*Petiole length.*—About 2.5 cm.

*Petiole diameter.*—About 0.2 cm to 0.3 cm.

*Petiole texture.*—Upper surface: Smooth. Lower surface: Smooth.

*Petiole color.*—Upper surface: Green, RHS 137C. Lower surface: Green, RHS 137D.

*Foliage fragrance.*—None.

Inflorescence description:

*Appearance.*—Daisy-type, composite inflorescence form. Disc and ray florets develop acropetally on capitulum.

*Natural flowering season*.—All year round in moderate climate. Flowering occurs between November and March outdoors in Israel.
*Flowering response time*.—About 7 weeks from planting.
*Flowering longevity*.—On the plant: Flowering of a single flower lasts about 20 days.
*Fragrance*.—None.
*Quantity of inflorescences and buds per plant*.—About 150 to 200.

Bud (about 15 to 20 days prior to opening):
*Length*.—About 0.5 cm.
*Diameter*.—About 0.7 cm to 0.8 cm.
*Shape*.—Round.
*Color*.—Apex: Greyed-green, RHS 197C. Base: Green, RHS 137D.
*Texture*.—Rough.

Inflorescence:
*Type*.—Solitary.
*Form*.—Daisy-like.
*Symmetry*.—Symmetric.
*Orientation at opening*.—Slanted upward.
*Size* (*including ray and disc florets*).—Depth (height): About 1.5 cm. Diameter About 3.5 cm to 4.0 cm. Disc diameter: About 1.0 cm.

Ray florets:
*Quantity per inflorescence*.—About 20 to 22 in a single whorl.
*Length*.—About 15 mm.
*Width*.—About 4 mm.
*Overall shape*.—Oblong.
*Shape at apex*.—Retuse.
*Shape at base*.—Attenuate.
*Margin*.—Entire.
*Texture*.—Upper surface: Smooth. Lower surface: Smooth.
*Orientation*.—Initially 90° from vertical, with development, close to 45° from vertical.
*Color* (*when opening*).—Upper surface: White, RHS N999D. Lower surface: White, RHS N999D.
*Color* (*when fully opened*).—Upper surface: White, RHS N999D. Lower surface: White, RHS N999D.

Disc florets:
*Quantity per inflorescence*.—About 150 to 200.
*Length*.—About 6 mm.
*Width*.—About 10 mm.
*Overall shape*.—Bell-shaped, campanulate.
*Shape at apex*.—Toothed.
*Shape at base*.—Wedge-shaped, cuneate.
*Margin*.—Entire.
*Texture*.—Upper surface: Smooth. Lower surface: Smooth.
*Color* (*when opening*).—Upper surface: Yellow-green, RHS N144A. Lower surface: Yellow-green, RHS 144C.
*Color* (*when fully opened*).—Upper surface: Yellow-green, RHS 153C. Lower surface: Yellow-green, RHS 153C.

Phyllaries:
*Quantity*.—About 15 to 17.
*Attachment*.—About 15 to 17 to the receptacle bottom.
*Length*.—About 2 mm to 3 mm.
*Width*.—About 1 mm.
*Overall shape*.—Oval.
*Shape at apex*.—Rounded.
*Shape at base*.—Obtuse.
*Margin*.—Entire.
*Texture*.—Upper surface : Smooth. Lower surface: Smooth.
*Color*.—Upper surface: Yellow-green, RHS 144C. Lower surface: Yellow-green, RHS 144B.
*Anythocyanin pigmentation of phyllaries limb*.—Absent.

Peduncle:
*Aspect*.—Upright, strong.
*Length*.—About 60 mm to 65 mm.
*Diameter*.—About 1 mm.
*Angle*.—About 80° from vertical.
*Texture*.—Smooth.
*Color*.—Yellow-green, RHS 146B.

Reproductive organs:

Androecium (on disc florets only):
*Stamens*.—Number: 5 (fused as tube). Arrangement: Didynamous. Type: Basifixed. Dehiscence of stamens: Extrose. Length: About 0.8 mm to 1.0 mm. Color: Yellow, RHS 13A.
*Anthers*.—Shape: Rounded. Length: About 0.5 mm. Color: Yellow, RHS 13A.
*Filaments*.—Length: About 5 mm. Color: Yellow-green, RHS 145 C.
*Pollen*.—Amount: Abundant. Pollen color: Yellow, RHS 13A. Pollination requirements: None.

Gynoecium (on ray florets):
*Pistils*.—Quantity per inflorescence: About 200. Length: About 5 mm.
*Stigma*.—Shape: Stringy. Width: About 2 mm. Color: Yellow, RHS 12B.
*Style*.—Shape: Terete. Length: About 2 mm.
*Ovary*.—Quantity: One per pistil. Shape: Ellipsoid. Position: Superior. Length: About 1.5 mm. Width: About 0.7 mm. Color: Yellow-green, RHS 149 D.

Seeds:
*Quantity per fruit*.—About 1.
*Shape*.—Oblong.
*Length*.—About 2.0 mm.
*Width*.—About 1.0 mm.
*Texture*.—Smooth.
*Color*.—Greyed-yellow, RHS 161A.

Fruit:
*Type*.—Achene.
*Shape*.—Oblong.
*Length*.—About 2.0 mm.
*Width*.—About 1.0 mm.
*Texture*.—Smooth.
*Color*.—Greyed-yellow, RHS 161A.

Disease/pest resistance: Resistance to disease and pests common to *Argyranthemum* has not been tested on plant grown under commercial conditions.

Disease/pest susceptibility: Susceptibility to disease and pests common to *Argyranthemum* has not been observed on plant grown under commercial conditions.

Temperature tolerance: Plants of the new *Argyranthemum* have exhibited good tolerance to draught, rain and wind, however, flowering may cease during hot periods (temperatures above 35° C.). Low temperature tolerance to 10° C.

What is claimed is:

1. A new and distinct cultivar of *Argyranthemum* plant named 'DANARGY27', as illustrated and described herein.

* * * * *